United States Patent [19]

Lentrichia et al.

[11] Patent Number: 4,960,692
[45] Date of Patent: Oct. 2, 1990

[54] ASSAY EMPLOYING BINDING PAIR MEMBERS ON PARTICLES AND ON A FILTER OR MEMBRANE

[75] Inventors: Brian B. Lentrichia, Mahwah, N.J.; Michael F. Turanchik, Stoney Point, N.Y.

[73] Assignee: Fisher Scientific Company, Pittsburgh, Pa.

[21] Appl. No.: 840,791

[22] Filed: Mar. 18, 1986

[51] Int. Cl.$^5$ .................. G01N 33/53; G01N 33/535; G01N 33/543; G01N 33/544
[52] U.S. Cl. ........................................ 435/7; 436/518; 436/528; 436/531; 436/533; 436/808; 435/810
[58] Field of Search .................... 435/7, 810; 436/518, 436/808, 528, 533

[56] References Cited

U.S. PATENT DOCUMENTS

| | | | |
|---|---|---|---|
| 4,115,535 | 9/1978 | Giaver | 436/526 |
| 4,200,690 | 4/1980 | Root et al. | 435/7 |
| 4,246,339 | 1/1981 | Cole et al. | 435/7 |
| 4,308,026 | 12/1981 | Mochida | 436/523 |
| 4,424,279 | 1/1984 | Bohn et al. | 436/534 |
| 4,459,361 | 7/1984 | Gefter | 436/523 |
| 4,486,530 | 12/1984 | David et al. | 435/7 |

FOREIGN PATENT DOCUMENTS 0070527 1/1983 European Pat. Off. .
0170746 2/1986 European Pat. Off. .

OTHER PUBLICATIONS

Pall Biotechnology Division, "Pall Biodyne TM Immounoaffinity Membrane" (Feb. 1985) Product Information Bulletin.
L. Blankenstein et al., "An Advanced Affinity Membrane for Immunodiagnostic Tests" Am Clin Prod Rev 33–41 (Nov. 1985).
Zuk et al., "Enzyme Immunochromatography" Clin. Chem. 31(7) pp. 1144–1150 (Nov. 1985).

Primary Examiner—Sam Rosen
Assistant Examiner—Janelle Graeter
Attorney, Agent, or Firm—Alan M. Doernberg

[57] ABSTRACT

An assay method and kit in which particles bearing a first reagent binding pair member (e.g., anti-digoxin antibody) react with a sample such that analyte binding pair member (e.g., digoxin) binds to the first reagent binding pair member. The reaction mixture is then passed through a filter or membrane or pore size sufficient to allow particles to pass through. A second reagent binding pair member (e.g., digoxin-albumin conjugate) is immobilized on the filter or membrane to trap preferentially either particles which have bound analyte binding pair members or particles which have not, leaving the other class of particles to pass through the filter for detection by resistive pulse techniques, by light absorbence or scattering, by enzymatic read-out (when the particles are enzyme-labeled) or otherwise.

16 Claims, No Drawings

ASSAY EMPLOYING BINDING PAIR MEMBERS ON PARTICLES AND ON A FILTER OR MEMBRANE

BACKGROUND OF THE INVENTION

The present invention relates to methods and kits for specific binding assays, e.g., immunoassays, involving binding pair members on suspendable particles.

Immunoassays involving suspendable particles (e.g., polystyrene latex) are well known, with the presence of analyte binding pair member affecting the binding of particles to one another. In manual assays, the agglutinated particles are observed or separate by gravity. In U.S. Pat. No. 4,202,665 to Wenz, et al (1980) and in copending application 733,688 of Jensen, et al., agglutinated particles act specifically in a centrifugal field. In copending application 733,689 of Lentrichia, et al, particles of two specific gravities bind one to the other in an amount affected by the analyte concentration. When first particles of one specific gravity are moved by centrifugal action, those second particles of the other specific gravity which are bound move with the first particles. See also U.S. Pat. No. 4,115,535 to Giaver (1978) for assays having two particles, each having a protein binding to the same analyte.

U.S. Patent 4,459,361 to Gefter (1984) discloses a particle immunoassay in which particles bind or agglutinate with other particles as a function of analyte ligand concentration. Filtration (e.g., through a 0.4 micrometer pore size filter) allows single particles (e.g., of 0.3 micrometer diameter) to pass through while duplexes and higher aggregates of particles are trapped by the filter. Particles passing through the filter can be visualized, or visibility can be enhanced by color, optical density, fluorescence or other properties of the particles or by enzymes attached to the particles (col. 4, line 42 - col. 5, line 4).

U.S. Pat. No. 4,424,279 to Bohn, et al (1984) discloses an assay method and plunger apparatus wherein large particles (20–30 micrometers diameter) bearing a binding pair member (e.g., antibody) are located in an apparatus compartment. Analyte binding pair member (e.g., antigen) and soluble labeled binding pair member (e.g., second antibody-enzyme) each enter the apparatus compartment for a reaction period and then liquids are withdrawn from the apparatus compartment by vacuum, with the particles retained by a coarse (e.g., 15–17 micrometer pore size) filter. Thereafter, particles remaining in the apparatus compartment are assayed for labels e.g., by addition of enzymatic reagents and cleaving the linkage between the enzyme and the second antibody.

Several references including L.A. Blankstein, et al., Am. Clin, Prod. Rev. 33–41 (Nov. 1985) and U.S. Pat. Nos. 4,200,690 to Root, et al. (1980), 4,246,339 to Cole, et al (1981) and 4,407,943 (1983) describe immunoassays in which an antibody or antigen is immobilized in a microporous membrane have pore size significantly large (0.65–5.0 micrometer) for either small molecules or small molecules and bacteria to migrate through the membrane. Thus, in U.S. Pat. No. 4,200,690 an antibody coated on such a membrane captures analyte antigen from crude sample. After washing, a second antibody conjugated to an enzyme (soluble conjugate) is introduced to bind specifically to bound analyte antigen. After washing, enzymatic read-out is compared to that from a similar membrane with an antibody thereon not specific for the analyte. U.S. Pat. No 4,407,943 to Cole, et al (1983) is similar.

U.S. Pat. No. 4,486,530 to David, et al, discloses immunoassays with monoclonal antibodies, especially of a sandwich geometry. Reference is made, however, at col. 15, lines 33–51 to an assay employing chromophore labeled antigen and monoclonal antibody bound to latex so that analyte antigen inhibits agglomeration and thus permits the chromophore to remain in solution where its fluorescence will not be quenched. Other inhibition assays where one binding pair member may be particle-bound are described in U.S. Pat. No. 4,308,026 to Mochida (1981).

BRIEF DESCRIPTION OF THE INVENTION

In the present invention, particles bearing a first reagent binding pair member react with a sample such that analyte binding pair member binds to the first reagent binding pair member. The reaction mixture is then passed through a filter or membrane of pore size sufficient to allow particles to pass through. A second reagent binding pair member is immobilized on the filter or membrane to trap preferentially either particles which have bound analyte binding pair members or particles which have not, leaving the other class of particles to pass through the filter for detection by resistive pulse techniques, by light absorbence or scattering, by enzymatic read-out or otherwise.

Accordingly, the present invention provides a method of determining (qualitatively or quantitatively) an analyte binding pair member in a biological sample which comprises the steps:

(a) contacting suspended particles bearing first reagent binding pair members complementary to analyte binding pair members with the biological sample under conditions under which the analyte binding pair members, if present, will bind to the first reagent binding pair members, and (b) passing the reaction mixture of the contacting step (a) through a filter having pore size sufficiently large for the particles to pass through the filter if not bound to the filter; the filter bearing second reagent binding pair members complementary either to the analyte binding pair members or to the first reagent binding pair members; and (c) detecting the particles passing through the filter as an indication of the presence and amount of analyte binding pair members in the biological sample.

The present invention also provides a kit for determining (qualitatively or quantitatively) an analyte binding pair member in a biological sample which comprises:

(a) a suspension of particles bearing first reagent binding pair members complementary to analyte binding pair members, (b) a filter having pore size sufficiently large for particles to pass through the filter if not bound to the filter, and (c) second reagent binding pair member immobilized to the filter which are complementary either to the analyte binding pair members or to the first reagent binding pair members.

DETAILED DESCRIPTION OF THE INVENTION

The present invention applies to qualitative or quantitative detection of various types of binding pair members, including antigens, haptens, antibodies, binding proteins, receptors, and nucleic acid sequences. For ease of presentation, assays for antigens or antibodies will be described first; comments about assays for other analytes will be described thereafter. The term "complementary" as to a first and second binding pair member is used in the sense of one being capable of specifically binding to other, generally by means of ionic interactions and/or hydrogen bonding. The term "competitive" as to a first and second binding pair member is used in the sense that each is complementary to a third binding pair member, and that binding of the first binding pair member to the third binding pair member reduces (or eliminates) the sites on the third binding pair member where the second binding pair member can bind, or otherwise (e.g., sterically) inhibits binding between the second and third binding pair member. The term "sandwich" is used in the sense that a third binding pair member can be bound simultaneously to a first binding pair member and to a second binding pair member, forming a bridge therebetween, generally without significant steric hindrance.

Two reagents used in the present invention are a suspension of particles bearing a first binding pair member and a filter or membrane bearing a second binding pair member. The particles can be of a variety of cellular, synthetic or inorganic types such as fixed erythrocytes, bacterial cells, viral particles, polystyrene latex particles, metallic sols, dyed chloesterol lecithin particles, charcoal, particulate dyes and bentonite particles. Preferred are the synthetic polymeric latex particles, and especially polystyrene latex particles. Such particles can be of a variety of sizes, e.g., 0.05–5.0 micron diameter, with particles of 0.1–1.5 micron diameter being preferred. While particles of relatively narrow particle size distribution can be used (e.g., 90% of the particles within 10% of median diameter), somewhat broader distributions are also acceptable.

The first binding pair member can be adsorbed or attached to the particles in a variety of known techniques, e.g., physical adsorption, carbodiimide chemical attachment or cross-linking with a mono- or bifunctional aldehyde. The particles may be precoated or simultaneously coated with materials such as albumin to inhibit non-specific adsorption or agglomeration of particles. The particles may further contain or have adsorbed thereon or attached thereto a label, such as fluorescent molecules, enzymes, dyes or radioisotopes. In the exemplary system described below, the first binding pair member is an antibody specific for digoxin.

In addition to directly attaching the label (e.g., the enzyme) to the particle, one can also attach the label to the binding pair member (e.g., the anti-digoxin antibody) or have the label (e.g., the enzyme) conjugated with one of avidin or biotin and have the other of avidin or biotin bound to the binding pair member (e.g., the anti-digoxin antibody) or to the particle (covalently or by adsorption) so as to provide indirect attachment via an avidin-biotin bridge.

The reagent containing second binding pair member is a membrane or filter having bound thereon the second binding pair member. Such membranes or filters have been often described as such for two applications: (1) affinity purification of the complementary binding pair member, or (2) diagnostic assays for the complementary binding pair member in which the remaining reagents are dissolved. Particularly preferred are the microporous membranes of U.S. Pat. Nos. 4,066,512, 4,200,690, 4,246,339 and 4,407,943, in which a polymeric membrane (e.g., nylon or poly(vinylidine fluoride)) is coated both with the second binding pair member and with an inert protein (e.g., zein) to retard non-specific adsorption. Pore sizes of the membrane should, for the present invention, be larger than the diameter of the particles and preferably at least about 400% of the mean diameter of the particles. Thus, when membranes of 5.0 micron pore sized are used, particles with mean diameter smaller than 5.0 microns could be used, but particles with mean diameter of about 1.25 microns or less are preferred. Similarly, when membranes (filters) of 3.0 micron pore size are used, the particles preferably have a mean diameter of 0.75 microns or less.

In an exemplary assay for digoxin (a hapten which is frequenty monitored as a therapeutic drug) the particles can bear anti-digoxin antibody (raised by the innoculation of an animal, e.g., rabbits, with a digoxin conjugate, e.g., digoxin-albumin). The membrane can in such case bear a digoxin-albumin conjugate. After contact of the particles with a sample (e.g., from a patient's serum), some of the particles will have antibody sites blocked with analyte digoxin. This reaction can reach equilibrium very quickly, and in most cases requires a minute or less to achieve either equilibrium or a sufficient degree of reaction. The more analyte digoxin is present, the more particles will have some or all antibody sites so blocked. When the reaction mixture is then passed through the membrane, those particles having few or no free antibody sites will pass preferentially through the filter; those particles having most or all of their antibody sites free will adhere to digoxin-albumin sites on the membrane and not pass through. This reaction is also very rapid, and can be conducted merely by passing the reaction mixture through the filter by the action of pressure or vacuum. With the proper loading of antibody on particles and proper level of particles/serum, each easily determined through routine experimentation, an assay system can be developed giving a measurable positive correlation between digoxin level in serum (over the range of interest) and particles in the eluant through the membrane. The present Examples illustrate dose-response curves in such instances, with the eluant particles measured by enzymatic read-out (Example 1), turbidimetric measurement (Example 2) or particle counting (which has been performed using the same latex reagent and treated filter as described in Example 2).

Several other exemplary systems according to the present invention have application in the use of the present invention to detect antibodies, nucleic acid sequences or multiepitopic antigens. Thus, for detecting antibodies, the complementary antigen can be on the particles and an antibody competitive with the analyte antibody can be on the membrane (filter). For detecting a target nucleic acid sequence, a complementary nucleic acid sequence can be on the particles and a competitive nucleic acid sequence can be on the membrane (see copending U.S.S.N. 790,671 of Ellwood, Diamond and Collins, filed Oct. 23,1985). For detecting a multivalent antigen (having, for example epitope-1 and epitope-2), anti-epitope-1 antibody can be on the particles and anti-epitope-2 antibody can be the membrane, so as to form a sandwich whereby increasing amounts of particles are retained with increasing amounts of analyte multiepitotic antigen.

In similar fashion, embodiments of the present invention of either a sandwich geometry or a competitive geometry can be used to detect haptens (including digoxin, theophylline, thyroxine, drugs of abuse and gentamycin), antigens (including HCG, LH, transferrin, CRP and CEA), viral agents (such as herpes, generically or of a particular type, hepatitis, generically or of a particular type and HTLV-III), tumor antigens, exotoxins, other proteins shed by bacterial or parasitic organisms, antibodies (including those against streptolysin-O, DNase-B, HTLV-III or rubella or those associated with infectious mononucleosis), viral DNA or RNA sequences, bacterial or parasitic DNA, mRNA or rRNA sequences, folate binding protein or thyroxin binding protein.

In general, it is preferred that the binding pair members on some particles not specifically bind to binding pair members on other particles.

EXAMPLES

Example 1

From a five square foot section of a "Biodyne" Immunoaffinity membrane (#BIA050C5, Pall Corporation) with a 5.0 micron pore size, was cut 13 mm diameter circles. The carboxylate-activated filters were then reacted by submersion in either a solution of 10 mg/ml BSA in PBS or 10 mg/ml BSA-digoxin conjugate in PBS for two hours at room temperature. The filters were then washed by incubation in PBS alone by the same method. After blotting the BSA and BSA-digoxin activated filters were allowed to air dry.

Unmodified polystyrene latex particles of 0.30 micron diameter (Japanese Synthetic Rubber Co., #G2203) were first adsorbed with whole anti-digoxin rabbit serum at 180 ug protein/mg latex in 0.05M phosphate buffer pH 7.8 by incubation at room temperature with gentle agitation for 2.5 hours. After washing the latex once by centrifugation in the same phosphate buffer, the partially adsorbed particles were then incubated in a 64 mg/ml solution of purified glucose oxidase (EC 1.1.3.4.) in phosphate buffer pH 7.8 for 10 hours at 4° C. After washing the latex repeatedly by centrifugation in PBS containing 10 mg/ml BSA (PBS/BSA), the particles were finally suspended to a concentration of 20 ug latex/ml (0.002%) in the same buffer.

The antigen-sensitized filters were placed in Swinney type holders fitted with 1 cc syringes. The latex reagent described above (0.25 ml of 0.002%) was then combined with 0.25 ml of PBS/BSA which would contain various concentrations of analyte, and the entire mixture passed through the filter and into a tube containing 0.30 ml of a substrate mixture containing 1.8% glucose, 8.7 units/ml horseradish peroxidase and 1.2 mM 4-aminoantipyrine. The entire mixture was agitated, incubated at 37° C. for five minutes and the absorbance read at 510 nm.

The digoxin sensitized filters retained about 80% of the total detected enzyme activity while the BSA-sensitized filters only retained about 28% (Table I). The difference reflects that number of latex particles specifically bound to the filter via digoxin immunoreactivity. The number of particles retained might also be detected by incubating the filter itself with the substrate mixture.

Sensitivity

Latex particles (0.49 um) were adsorbed with anti-digoxin serum and glucose oxidase as described above. Then 0.25 ml of a 0.0132% (w/w) suspension of the latex was mixed with 0.25 ml PBS/BSA buffer containing various concentrations of digoxin before being passed through the digoxin-sensitized filter and into 0.30 ml of a substrate solution (total volume=0.80ml). After mixing and incubation of the reaction at 37° C. for five minutes, the optical density was recorded at 510 nm.

The assay was sensitive to at least 5 ng/ml (Table II). Only 7% of the total activity was retained in the membrane due to non-specific interaction (unfiltered control vs. BSA filter).

TABLE I

| Specific Retention of Immunoreactive Latex Particles By Digoxin Sensitized Membranes. | | |
|---|---|---|
| | $OD_{510}$ | % Latex Retained |
| Digoxin Filter | 0.051 | 80 |
| BSA Filter | 0.165 | 28 |
| No Filter | 0.232 | 0 |

TABLE II

| Sensitivity of Membrane - Latex Assay. | | |
|---|---|---|
| ng Digoxin/ml | $OD_{510}$ | % Latex Retained |
| 0 | 0.093 | 78 |
| 5 | 0.279 | 33 |
| 10 | 0.289 | 31 |
| 50 | 0.346 | 17 |
| 100 | 0.355 | 15 |
| BSA filter | 0.387 | 7 |
| unfiltered control | 0.416 | 0 |

Example 2

Unmodified polystyrene latex particles of 1.09 micron diameter (Japanese Synthetic Rubber Co. #G2101) were adsorbed with whole anti-digoxin rabbit serum at 200 ug protein/mg latex under the same conditions as those described in Example 1. Following this sensitization of the particles with antibody, they were washed by centrifugation repeatedly in PBS/BSA and resuspended finally to a concentration of 0.003% (w/w) as determined by optical density at 650 nm. A section of "Biodyne" immunoaffinity membrane. (#BI050C5, Pall Corporation) with a 5.0 micron average pore size, was cut into 13 mm diameter circles and activated with a BSA-digoxin conjugate also as described in Example 1.

To perform the assay, 1.5 ml of the 0.003% suspension of latex was mixed with 0.5 ml of a digoxin-containing solution in PBS and the mixture passed through the immunoaffinity membrane using a 5 cc syringe. The optical density of the filtrate was then measured at 650 nm in a spectrophotometer.

As seen in Table III, over a seven fold greater OD was observed in the presence of 10 ng/ml of the analyte as compared to the OD found in the absence of any digoxin. In addition, the number of particles passing through the filter continued to increase with increasing concentrations of digoxin. Up to a 14 fold increase at 100 ng/ml was found, a concentration close to saturating for the particle-immobilized binding sites.

TABLE III

| Digoxin Immunoassay By Turbidimetric Membrane-Latex Method (Manual) | |
|---|---|
| ng Digoxin/ml | $OD_{650}$ |
| 0 | 0.027 |
| 10 | 0.197 |
| 50 | 0.266 |
| 75 | 0.352 |

TABLE III-continued

Digoxin Immunoassay By Turbidimetric
Membrane-Latex Method (Manual)

| ng Digoxin/ml | OD$_{650}$ |
|---|---|
| 100 | 0.380 |

Example 3

Reagent Formulation

Biodyne Immunoaffinity filters (5.0 um pore size) were first sensitized with human chorionic gonadotropin (HCG) by the following procedure: About 35, 13 mm diameter filters were placed individually in a 2 ml solution containing 4.5 mg/ml of HCG purified by gel filtration and DEAE ion exchange chromatography (8409 IU/mg solid) in PBS. After soaking at room temperature for one (1) hour, the filters were transferred into a 250 ml solution of PBS containing 10 mg/ml bovine serum albumin (BSA) and 0.1% sodium azide and soaked for an additional 20 minutes. The filters were finally rinsed by immersion in distilled water, blotted on filter paper and allowed to dry at room temperature.

Latex particles of 0.49 um diameter (JSR #U0403) were sensitized with anti-beta-HCG monoclonal antibody and glucose oxidase by the following procedure. Particles which had been washed in 0.01M sodium phosphate buffer pH 7.8 were suspended in the same buffer to a final concentration of about 10%, and 20 mg (0.20 ml) were transferred to a small, glass screw-cap vial. Then, 0.10 ml (0.56 mg protein) of a purified monoclonal anti-beta-HCG antibody (Maritime Chemical Corp.) was added. After incubation at 4° C. overnight, the latex sample was washed once by centrifugation in phosphate buffer, resuspended in 0.10 ml of the same buffer, and 10 mg of solid, purified glucose oxidase (Boehringer Mannheim) added for a total volume of about 0.20 ml. The reaction mixture was incubated for one (1) hour at room temperature, washed twice with 10 mg/ml BSA in PBS by centrifugation and resuspended finally to a concentration of 0.88% (8.8 mg latex/ml) in PBS/BSA containing 0.1% azide.

Assay Procedure

A fresh substrate mixture as described in Example 1, was prepared and 0.5 ml placed in each of 5, 12×75 mm glass test tubes. The HCG-sensitized filters described above were placed in Swinney type filter holders, each fitted with 1 cc tuberculin syringes without plungers. Latex-analyte mixtures were prepared by mixing 0.01 ml of 0.88% latex with 0.69 ml of containing the various concentrations of purified HCG in PBS/BSA buffer shown in Table IV. (Final latex concentration=0.013%). After standing at room temperature for 2 to 3 minutes, the latex suspensions were individually transferred to different syringes fitted with filters and forced into the test tubes containing substrate.

The absorbance of each suspension at a wavelength of 510 nm was determined following a five minute incubation in a 37° C. water bath, by placing the test tube directly into a Spectronic 21 spectrophotometer (Bausch and Lomb).

A standard curve for HCG by the method described above is shown in Table IV. The greatest portion of the total difference in OD obtained was seen at a concentration of 5 IU/ml (84%) with a gradual increase in OD up to 40 IU/ml.

TABLE IV

Immunoassay for beta-HCG Using the Enzyme-Enhanced
Latex - Immunoaffinity Filter Method

| IU HCG/ml | OD$_{510}$ |
|---|---|
| 0 | 0.189 |
| 1 | 0.198 |
| 5 | 0.374 |
| 10 | 0.381 |
| 40 | 0.410 |

What is claimed is:

1. A method of determining an analyte binding pair member in a biological sample which comprises the steps:
   (a) contacting suspended particles bearing first reagent binding pair members complementary to analyte binding pair members with the biological sample under conditions under which the analyte binding pair members, if present, will bind to the first reagent binding pair members, and
   (b) passing the reaction mixture of the contacting step (a) through a filter having pore size sufficiently large for the particles to pass through the filter if not bound to the filter; the filter bearing second reagent binding pair members complementary either to the analyte binding pair members or to the first reagent binding pair members; and
   (c) detecting the particles passing through the filter as an indication of the presence and amount of analyte binding pair members in the biological sample.

2. The method of claim 1 wherein the second reagent binding pair members are complementary to the first reagent binding pair members and are competitive with the analyte binding pair members for binding sites on the first binding pair members.

3. The method of claim 2 wherein the first reagent binding pair members are antibodies.

4. The method of claim 3 wherein the second reagent binding pair members and analyte binding pair members are haptens.

5. The method of claim 3 wherein the second reagent binding pair members and analyte binding pair members are antigens.

6. The method of claim 1 wherein the second reagent binding pair members are complementary to the analyte binding pair members at a binding site of the analyte binding pair member different from the binding site of the analyte binding pair member which binds to the first reagent binding pair members.

7. The method of claim 6 wherein the analyte binding pair member is an antigen having at least two distinct epitopes, and wherein the first and second reagent binding pair members are antibodies specific for different epitopes of the antigen.

8. The method of claim 6 wherein the analyte binding pair member is an antibody.

9. The method of claim 8 wherein the first reagent binding pair member is an antigen or hapten for which the analyte antibody is specific and wherein the second reagent binding pair member is an antibody specific for the analyte antibody or for immune complexes including the analyte antibody.

10. The method of claim 1 wherein the particles are of diameter 0.05 to 5 microns and wherein the filter is of pore size at least 200% of the diameter of the particles.

11. The method of claim 1 wherein the detecting step (c) comprises passing the eluant which has passed through the filter through an orifice and measuring the impedance through the orifice.

12. The method of claim 1 wherein the detecting step (c) comprises measuring the absorbence of the eluant which has passed through the filter.

13. The method of claim 1 wherein the particles are fluorescent and the detecting step (c) comprises measuring the fluorescence of the eluant which has passed through the filter.

14. The method of claim 1 wherein the particles bear an enzyme and the detecting step (c) comprises admixing the eluant which has passed through the orifice with reagents for the enzyme.

15. A method of determining an analyte binding pair member in a biological sample which comprises the steps:
(a) contacting suspended particles bearing first reagent binding pair members complementary to analyte binding pair members with the biological sample under conditions under which the analyte binding pair members, if present, will bind to the first reagent binding pair members, and
(b) passing the reaction mixture of the contacting step (a) through a filter having pore size sufficiently large for the particles to pass through the filter if not bound to the filter; the filter bearing second reagent binding pair members complementary either to the analyte binding pair members or to the first reagent binding pair members; and
(c) detecting the particles bound by the filter as an indication of the presence and amount of analyte binding pair members in the biological sample.

16. A kit for determining an analyte binding pair member in a biological sample which comprises:
(a) a suspension of particles bearing first reagent binding pair members complementary to analyte binding pair members,
(b) a filter having pore size sufficiently large for particles to pass through the filter if not bound to the filter, and (c) second reagent binding pair member immobilized to the filter which are complementary either to the analyte binding pair members or to the first reagent binding pair members.

* * * * *